United States Patent

Haynes et al.

[11] Patent Number: 5,985,641
[45] Date of Patent: *Nov. 16, 1999

[54] NON-INFECTIOUS, REPLICATION-IMPAIRED, IMMUNOGENIC HUMAN IMMUNODEFICIENCY VIRUS TYPE 1 RETROVIRUS-LIKE PARTICLES WITH MULTIPLE GENETIC DEFICIENCIES

[75] Inventors: Joel Haynes, Newmarket; Michel Henri Klein, Willowdale; Benjamin Rovinski, Thornhill; Shi Xian Cao, Etobicoke, all of Canada

[73] Assignee: Connaught Laboratories Limited, North York, Canada

[*] Notice: This patent is subject to a terminal disclaimer.

[21] Appl. No.: 08/467,975

[22] Filed: Jun. 6, 1995

Related U.S. Application Data

[62] Division of application No. 08/239,427, May 6, 1994, Pat. No. 5,571,712, which is a division of application No. 07/839,751, filed as application No. PCT/CA90/00350, Dec. 10, 1990, Pat. No. 5,439,809.

[30] Foreign Application Priority Data

Oct. 13, 1989 [GB] United Kingdom ............... 8912123

[51] Int. Cl.⁶ ............... C12N 7/04; C12N 15/00; A61K 39/21
[52] U.S. Cl. ............... 435/236; 435/320.1; 424/188.1; 424/208.1
[58] Field of Search ............... 424/188.1, 208.1; 435/236

[56] References Cited

U.S. PATENT DOCUMENTS 5,324,645 6/1994 Takahara et al. ............... 435/172

FOREIGN PATENT DOCUMENTS

| 0386882 | of 0000 | European Pat. Off. . |
|---|---|---|
| 0241239 | 10/1987 | European Pat. Off. . |
| 0315459 | 5/1989 | European Pat. Off. . |
| 0335635 | 10/1989 | European Pat. Off. . |
| 0381146 | 8/1990 | European Pat. Off. . |
| 2181435 | of 0000 | United Kingdom . |
| WO 89/12095 | of 0000 | WIPO . |
| WO 88/03562 | 5/1988 | WIPO . |

OTHER PUBLICATIONS

D.D. Loeb et al, "Complete mutagenesis of the HIV–1 protease", pp. 397–400—see Abstract, Nature, vol. 340, No. 6232, Aug. 3, 1989.

Gowda, S. et al, J. Virol. 63(3):1451–1454, Mar. 1989.

Flexner, C. et al, Virology, 166:339–349, Oct. 1988.

Mazzara, G. et al, Abstract: Int. Conf. AIDS, Montreal, Canada, Jun. 4–9, 1989.

Shaw et al., "Eitology of AIDS: Virology, Molecular Biology, and Evolution of Human Immunodeficiency Viruses," in AIDS: Etiology, Diagnosis, Treatment, and Prevention, Second Edition, DeVita et al., eds., J. B. Lippincott Company, Philadelphia, p. 14 and 1988.

Rovinski et al., 1992, J. Virol. 66:4003–4012.

Haynes et al., 1991, AIDS Res. Hum. Retro. 7:17–27.

Karacostas et al., 1989, Proc. Natl. Acad. Sci. USA 86:8964–8967.

*Primary Examiner*—Laurie Scheiner
*Assistant Examiner*—Jeffrey S. Parkin
*Attorney, Agent, or Firm*—Sim & McBurney

[57] ABSTRACT

An immunogenic retrovirus-like particle which is non-infectious and non-replicating and which is useful as a candidate vaccine component against retroviral infections, including AIDS and ATLL, is produced by genetic engineering. A DNA molecule comprising a retroviral genome devoid of long terminal repeats is incorporated into an expression vector, which is introduced into mammalian cells for expression of the retrovirus-like particle.

8 Claims, 12 Drawing Sheets

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
      (A) LENGTH: 92 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
GATCTCGGAC CGCCTACAAT AAAAGAAAAA GGATACATAT AGGAAGCCTG GCGGATGTTA        60

TTTTCTTTTT CCTATGTATA TCCTGGTCCC TC                                      92
```

(2) INFORMATION FOR SEQ ID NO:2:

(i) SEQUENCE CHARACTERISTICS:
      (A) LENGTH: 88 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:2:

```
CCAGGGAGAG CATTTTATAC AACAAAAAAT ATAATAGGAA CGCGTATCGT AAAATATGTT      60

GTTTTTTATA TTATCCTTGC GCATCTAG                                        88
```

NON-INFECTIOUS, REPLICATION-IMPAIRED, IMMUNOGENIC HUMAN IMMUNODEFICIENCY VIRUS TYPE 1 RETROVIRUS-LIKE PARTICLES WITH MULTIPLE GENETIC DEFICIENCIES

This is a divisional of application Ser. No. 08/239,427 filed May 6, 1994 (now U.S. Pat. No. 5,571,712) which itself is a division of U.S. patent application Ser. No. 07/839,751 filed Jun. 15, 1992 (now U.S. Pat. No. 5,439,809), which was the National Stage of International Application No. PCT/CA90/00350, filed Dec. 10, 1990.

FIELD OF INVENTION

The present invention relates to the preparation of human retrovirus-like particles, specifically HIV-like particles, which are immunogenic and non-infectious. These preparations will serve as candidates for whole-virus-like vaccines for human retrovirus diseases and should not be subject to the ethical concerns regarding the production of classical whole-virus vaccines from infectious virus preparations.

BACKGROUND TO THE INVENTION

Among all diseases caused by retroviruses in humans and animals, the acquired immunodeficiency syndrome (AIDS) and the adult T-cell leukemia-lymphoma (ATLL) represent the most dramatic human diseases due to HIV and HTLV-1 retroviruses, respectively. The etiologic agent of the acquired immune deficiency syndrome (AIDS) is a human retrovirus termed human immunodeficiency virus (HIV) of which there are presently two major subgroups, HIV-1 and HIV-2. These viruses are responsible for an ever widening world-wide epidemic of immune deficiency and central nervous system (CNS) disorders characterized by a slow, yet progressive, degeneration of immune and CNS functions. HIV-1 affects mainly North America, Western Europe, Haiti and Central Africa while HIV-2 is found predominantly in West African countries. The earliest symptoms of HIV infection include an acute influenza-like syndrome which persists for 2 to 3 weeks. Several weeks to many months or years following infection, lymphadenopathy and/or progressive depletion in CD4+ T-helper lymphocytes becomes apparent and disease evolves to the point where immune deficiency becomes manifest. The diagnosis of HIV infection is confirmed by laboratory tests which include the detection of HIV-specific antibodies and/or HIV antigens in patient sera, and the isolation of infectious virus from patients body fluids or cells. A similar disease is observed in rhesus macaques infected with the simian acquired immunodeficiency virus (SIV).

Immune deficiency in HIV infection is characterized by opportunistic infections with microbial agents which are not normally associated with disease in otherwise healthy individuals. The severity of these infections is exacerbated by the loss of helper T-cell function, which, when combined with other symptoms, such as diarrhoea and weight loss, leads to a general wasting syndrome. Death usually results from one or more opportunistic infections. As mentioned above, CNS involvement is another manifestation of AIDS and can be the result of direct HIV-induced neurological disease as well as that of opportunistic infections.

The predominant host cells for HIV in infected individuals are the CD4+ T-helper cell and the monocyte/macrophage. However, more and more evidence points to the fact that HIV can infect a wide variety of cell types, CD4+ and CD4−, both in vivo and in vitro. These cell types include those of the haematopoietic system, the central nervous system, the gastrointestinal tract, and skin. This wide host cell tropism most likely accounts for the plethora of symptoms and the severity of disease associated with HIV infection.

HIV-1 and 2 have been the subject of massive and unprecedented research efforts in recent years in a number of areas including vaccine strategies. The development of an efficacious vaccine for prevention of HIV infection, is of considerable importance as it can be easily recognized that prevention of infection is the best way to combat any infectious disease.

Various strategies are currently being used in attempts to develop an effective vaccine against AIDS. Some of these strategies are briefly outlined along with their respective advantages and disadvantages.

A subunit HIV vaccine consists of one or more purified HIV immunogens, either obtained from disrupted whole virus or produced in genetically engineered eukaryotic or bacterial expression systems. An important advantage of this type of vaccine is the relative ease with which these products can be produced. However, this advantage can be countered by the fact that subunit vaccines only contain a subset of HIV antigenic determinants, which in some cases can lead to a less than optimal immune response. Moreover, viral protein subunits may adopt different spatial conformations when extracted from the context of the whole-virus particle. This may affect the structure of important conformational epitopes and result in inefficient immune responses.

Live recombinant virus vaccines consist of a non-pathogenic virus, such as vaccinia or adenovirus, which has one or more non-essential genes replaced by a nucleotide sequence encoding one or more HIV antigens. Live recombinant viruses can often induce efficient immune responses to single subunits of a particular pathogenic virus. However, as with subunit vaccines, recombinant virus vaccines express only a fraction of the total antigens of a given virus which can be disadvantageous when highly efficient immune responses are required.

Future vaccines may consist of synthetic peptides containing multiple epitopes of a given pathogen. These peptides, coupled to a carrier protein and combined with an appropriate adjuvant, are potentially capable of eliciting good and lasting humoral and cellular immune responses against multiple components of a pathogen. The development of an efficacious synthetic peptide vaccine for AIDS is likely to require the full identification of all the functionally important immunological determinants of HIV-1 and HIV-2, a task which may not be completed in the very near future. An important disadvantage of peptide vaccines is the difficulty to produce synthetic molecules mimicking conformational epitopes (immunological determinants which are formed by distant amino acid residues brought together in space by protein folding). If conformational epitopes are important for protection against a particular infectious agent, it is unlikely that traditional peptide vaccine designs will prove successful.

Inactivated, whole-virus vaccines consist of a purified preparation of intact particles from a given viral pathogen which has been rendered non-infectious by chemical or physical means. The inherent advantages of these vaccines are their relative ease of production and the fact that all or most of the important immunological epitopes of the virus are present. However, a major disadvantage of these vaccines is that infectious virus must be propagated on a large scale, thereby exposing production workers to significant risks, depending on the nature of the pathogen. Equally important is the fact that the virus must be rendered completely non-infectious. This poses ethical problems since it is extremely difficult to demonstrate that all infectious genetic material has been removed. Moreover, extensive inactivation regimes to kill all infectious viruses are likely to destroy or alter various immunological epitopes, thereby compromising the immunogenicity of the vaccine.

This invention describes a method to produce non-infectious, retrovirus-like particles as the basis for a candidate human vaccine against AIDS. This invention is also applicable to the production of similar particles serving as a candidate vaccine to other retrovirus diseases which include, but are not limited to, the simian acquired immune deficiency syndrome caused by the simian immunodeficiency virus (SIV), and certain forms of human T-cell leukemia-lymphoma caused by the human T-cell leukemia virus I (HTLV-1).

A non-infectious retrovirus-like particle of this nature does not contain any infectious RNA and has the advantage of including all or part of the major viral antigens in their native configuration. The production of such a particle does not obligatorily require physical or chemical inactivation, thus avoiding the possible destruction of important immunological determinants. The ability of this particle to elicit potent immune responses to native viral proteins without any risk of inducing infection and disease makes it an important new candidate vaccine for evaluation in animal models and humans.

SUMMARY OF INVENTION

This invention describes a general method for the production of human retrovirus-like particles, specifically HIV-like particles, which are immunogenic and non-infectious. This preparation of genetically engineered HIV-like particles will serve as a candidate "whole-virus" vaccine for AIDS and should not be subject to the specific ethical concerns regarding the production of classical whole-virus vaccines from infectious virus preparations. It should be noted that the methodologies developed here for the AIDS virus are directly applicable to all human and non-human retroviruses and can be used to produce any retroviral candidate vaccine, including, but not limited to, the AIDS virus, and not limited to human pathogens. Furthermore, the same methodologies can be used to produce non-infectious retroviral particles to serve as antigens in diagnostic immunoassays for retroviral diseases. For the purpose of clarity, the discussion here pertains to actual examples employing the AIDS virus, but it is to be assumed that this invention covers all retroviruses.

The present invention describes the engineering of cultured cells to produce retroviral proteins which self-assemble into virus-like particles in the absence of the production of an infectious retrovirus genomic RNA molecule. A virus-like particle can be defined here as a defective virion which is incapable of infecting a host cell due to the presence of one or more genetic modifications of viral genes or other genetic elements which are functionally critical at some stage of the virus life cycle. Virus-like particles may or may not contain all of the viral proteins normally found in infectious virions and may or may not contain RNA. If RNA is contained within the particle, it will be incapable of infecting a host cell.

In the present examples pertaining to HIV, the production of non-infectious virus-like particles required the isolation of a DNA fragment from the HIV provirus containing relevant protein coding information and deficient in genomic elements required for replication and transcription of the retrovirus genome. This DNA fragment was linked to a heterologous promoter and transfected into a cultured cell line to allow for the expression of HIV-1 proteins and their assembly into virus-like particles. The unique features of this invention are described in detail below but centre on the fact that the present invention consists of a preparation of virus-like particles, which will not require chemical inactivation, and which can serve as a candidate vaccine for retroviral pathogens. Moreover, the method allows for the production of non-infectious virus-like particles containing modifications in one or more viral proteins so as to enhance the immunogenicity of the particles. Thus, the resultant candidate vaccine will represent a safe preparation of virus-like particles containing an optimized set of immunological epitopes necessary for stimulating a potent immune response.

The safety of genetically engineered, non-infectious HIV-like particles can be guaranteed by the genetic engineering steps employed to produce these particles. Viral genetic elements required for replication are eliminated and a variety of genetic modifications can be introduced in the viral DNA sequences to be inserted into the producing cell line. These mutations can affect gene functions, gene products or genetic elements required for viral infectivity but not involved in the synthesis of the major viral proteins required for particle assembly or immunogenicity. With this strategy in hand, it becomes apparent to those skilled in the art that expression vectors employed to produce such non-infectious particles will not yield infectious viruses.

The techniques for producing a preparation of safe, non-infectious virus-like particles stem from knowledge which is available to those skilled in the art, but which has been applied here in a unique fashion to produce whole virus-like particles devoid of infectious HIV viral RNA or RNA which can be replicated into double-stranded DNA in a recipient cell. We have developed an expression system for HIV antigens which results in the production of the major HIV-1 antigens in an engineered cell in the absence of the production of an infectious genomic RNA molecule. We have demonstrated co-expression of the envelope and core antigens and provide evidence that these products are assembled into retrovirus-like particles and can be purified by means employed to purify normal, infectious preparations of HIV particles. In addition, these purified virus-like particles induce efficient HIV-1 specific antibody responses in immunized mice and cross-reactivity with other HIV strains, including HIV-2.

It is important to note that HIV-like particles and the cell lines used to produce these particles described here are significantly different from prior art retroviral studies involving the insertion of retrovirus genomes into cultured cell lines. Prior art experiments involved the construction of cell lines expressing murine retroviral proteins capable of packaging defective retroviral genomes carrying foreign genes. The packaging of defective retroviral genomic RNA molecules carrying foreign genes into virus particles allows for the efficient introduction of these RNAs into recipient cells. Once transduced into recipient cells, these recombinant viral RNAs become reverse transcribed into double-stranded DNA and integrated into the chromosomes of the cell, thereby genetically transforming the recipient cell. In the invention described here, the use of HIV-1 expression vectors devoid of long terminal repeat (LTR) elements results in the production of non-infectious virus-like particles which are intended for use as a vaccine and not for the transduction of recombinant retroviral RNA molecules into recipient cells for the purpose of genetic transformation. Indeed, in the present invention, RNA packaging into virus particles can be minimized and any RNA which is packaged cannot undergo the process of reverse transcription. Therefore, the present invention differs from prior art studies of retrovirus protein expression in the intended uses, methods employed, and the nature and characteristics of the resultant products.

As indicated above, the final products of the present invention are preparations of virus-like particles which are non-infectious due to the absence of an infectious retrovirus genome within the particles. Moreover, the present invention allows for genetic manipulations to optimize the immunogenicity of the particles and vaccine efficiency in immunized recipients. It is envisioned that significant alterations can be made to certain viral protein components of the genetically engineered particles through alterations in the DNA sequences encoding these components. These alterations are likely to involve the insertion of extra copies of various important immunological epitopes into virus protein regions, which are not critical for particle assembly, to generate candidate multivalent chimeric vaccines. Additional alterations might involve the deletion of certain protein regions which may be immunosuppressive or lead to the production of autoimmune disorders or enhancing antibodies. The alterations would be designed so as to avoid interference with particle assembly and create modified particles capable of eliciting an optimized immune response. The invention also allows for the production of hybrid viral particles containing antigens from multiple strains of a given infectious virus, or even from different viruses altogether.

In summary, an invention is described which entails the expression of normal or modified retroviral proteins in a cultured cell line for the intended purpose of producing non-infectious, assembled virus-like particles as a candidate vaccine. The invention describes the use of stably engineered cell lines using inducible and constitutive promoters and an example of one method to produce such particles. It is not to be assumed that the genetic engineering examples described here are the only means of expressing non-infectious retrovirus-like particles for vaccine use.

GENERAL DESCRIPTION OF THE INVENTION

Figure 1:
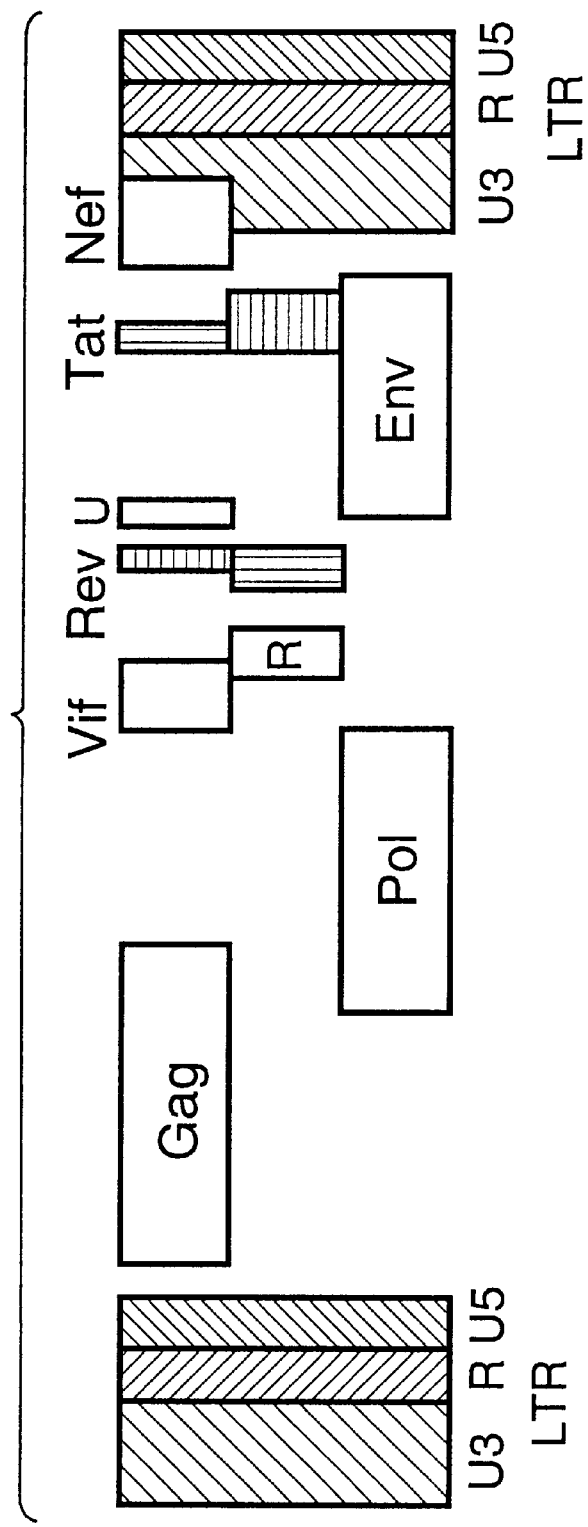
FIG. 1 shows a genetic map of the provirus of HIV strain LAV-1$_{BRU}$ which indicates the relative locations of the long terminal repeats (LTRs), the major protein coding sequences (gag, pol, and env) and the remaining open reading frames which encode minor structural and/or regulatory proteins (vif, rev, vpu, vpr, tat, and nef)
Figure 2:
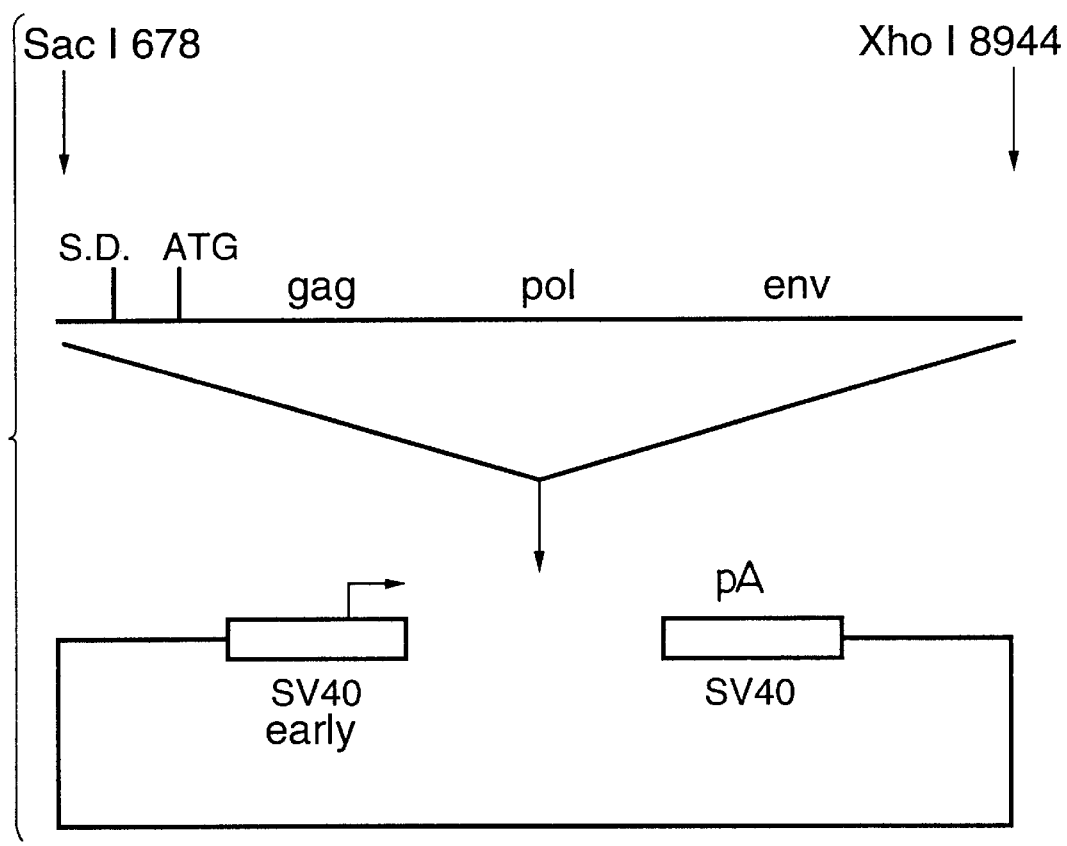
FIG. 2 shows a map of the HIV expression construct pHIV-SV which contains an 8.3 kb SacI-XhoI fragment from the LAV-1$_{BRU}$ genome. This fragment, which lacks LTR elements, was inserted into an expression vector containing the SV40 virus early promoter and late polyadenylation site.

FIG. 1 shows a functional map of the HIV-1 provirus indicating the location of various genes as well as the long terminal repeat (LTR) elements which are required for retroviral gene expression and genome replication. In the present invention, we have demonstrated that it was possible to produce HIV-1-like particles in transiently transfected monkey COS cells by inserting an 8.3 Kb SacI-XhoI DNA fragment from the provirus of LAV-1$_{BRU}$ into a simple eukaryotic expression vector employing the SV40 virus early promoter (FIG. 2). The proviral fragment employed contained the viral protein coding information found between the LTR elements and, therefore, lacked the genetic elements necessary for the reverse transcription of any RNA molecule transcribed from this fragment. Upon transfection of this vector into COS cells, HIV-1 protein expression was confirmed by metabolic labelling and immune precipitation, by Western blot analysis of pelleted material using a specific anti-HIV antiserum and detection of reverse transcriptase (RT) activity in the supernatant of transfected cells. Evidence for the formation of HIV-like particles was obtained by sucrose density gradient centrifugation of the high molecular weight material released in the supernatant of transfected cells. In this experiment, RT activity was shown to band at a density similar to that of intact retrovirus particles. It was further established that SIV-like particles could be engineered using the same method.

Figure 3:
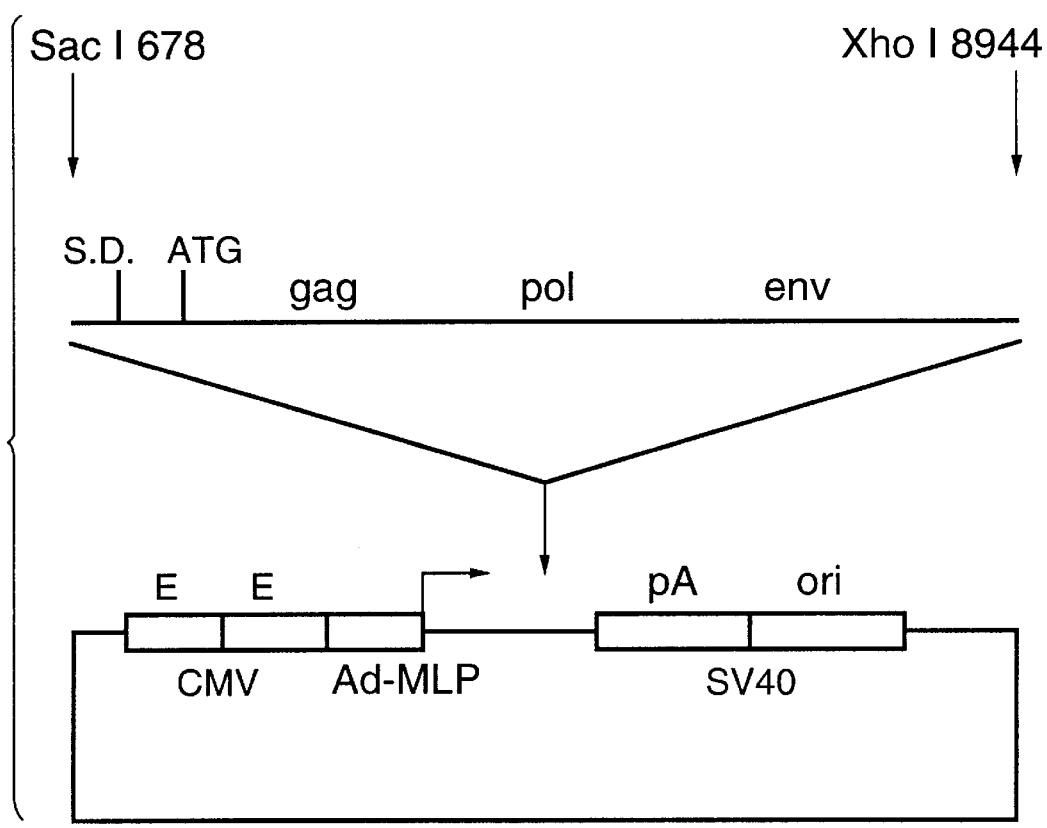
FIG. 3 shows a map of the HIV expression construct pHIV-CHO-SV which contains an 8.3 kb SacI-XhoI fragment from the LAV-1$_{BRU}$ genome. This fragment, which lacks LTR elements, was inserted into an expression vector containing the adenovirus major late promoter, two copies of the human cytomegalovirus immediate early enhancer, the SV40 virus late polyadenylation site, and the SV40 virus origin or replication. The latter element was inserted to allow for transient expression in monkey COS cells.

To establish stably engineered cell lines for more efficient production of non-infectious HIV-1-like particles, HIV-1 protein coding information was inserted into an expression vector employing the adenovirus major late promoter and transfected into COS cell along with a plasmid specifying resistance to the antibiotic G418 (FIG. 3). After examination of a number of G418 resistant cell clones, several were identified which constitutively produced high molecular weight material containing RT activity in association with major HIV-1 antigens. That actual virus-like particles were being produced was demonstrated by sucrose density gradient centrifugation and electron microscopic analysis. The latter revealed the presence of virus-like particles budding from the plasma membrane of transfected cells.

To demonstrate the potential for non-infectious HIV-1-like particles to function as a candidate vaccine, mice were immunized with a preparation of non-infectious HIV-1-like particles produced by stably transfected COS cells. In these experiments, particles were purified by sedimentation and sucrose banding and used as immunogens. After two injections, an efficient antibody response against various HIV-1 proteins and peptides was observed and virus neutralizing activity was detected for two HIV-1 strains. After a third injection, HIV-1 specific antibodies showed cross-reactivity with the envelope glycoprotein of HIV-2.

Figure 10:
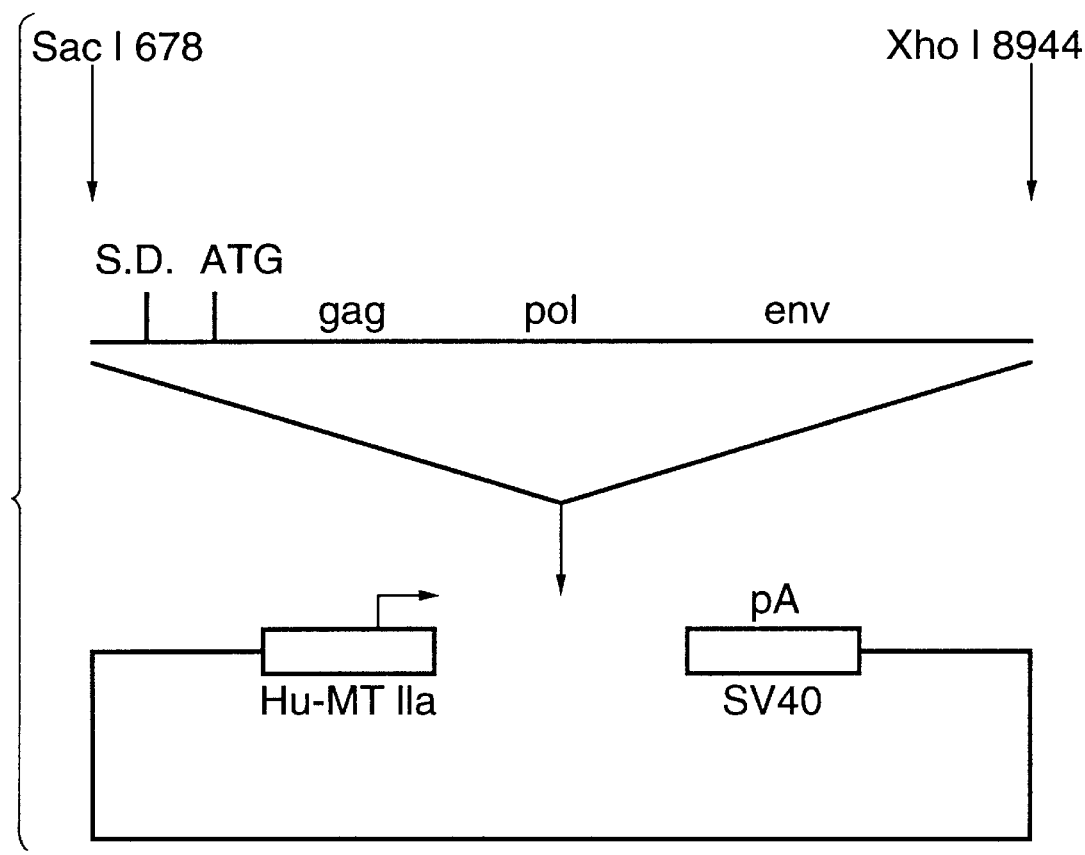
FIG. 10 shows a map of the HIV expression plasmid pMT-HIV which is similar to the pHIV-SV vector shown in FIG. 2. pMT-HIV contains the human metallothionein IIa promoter in place of the SV40 virus early promoter used in pHIV-SV.
Figure 11:
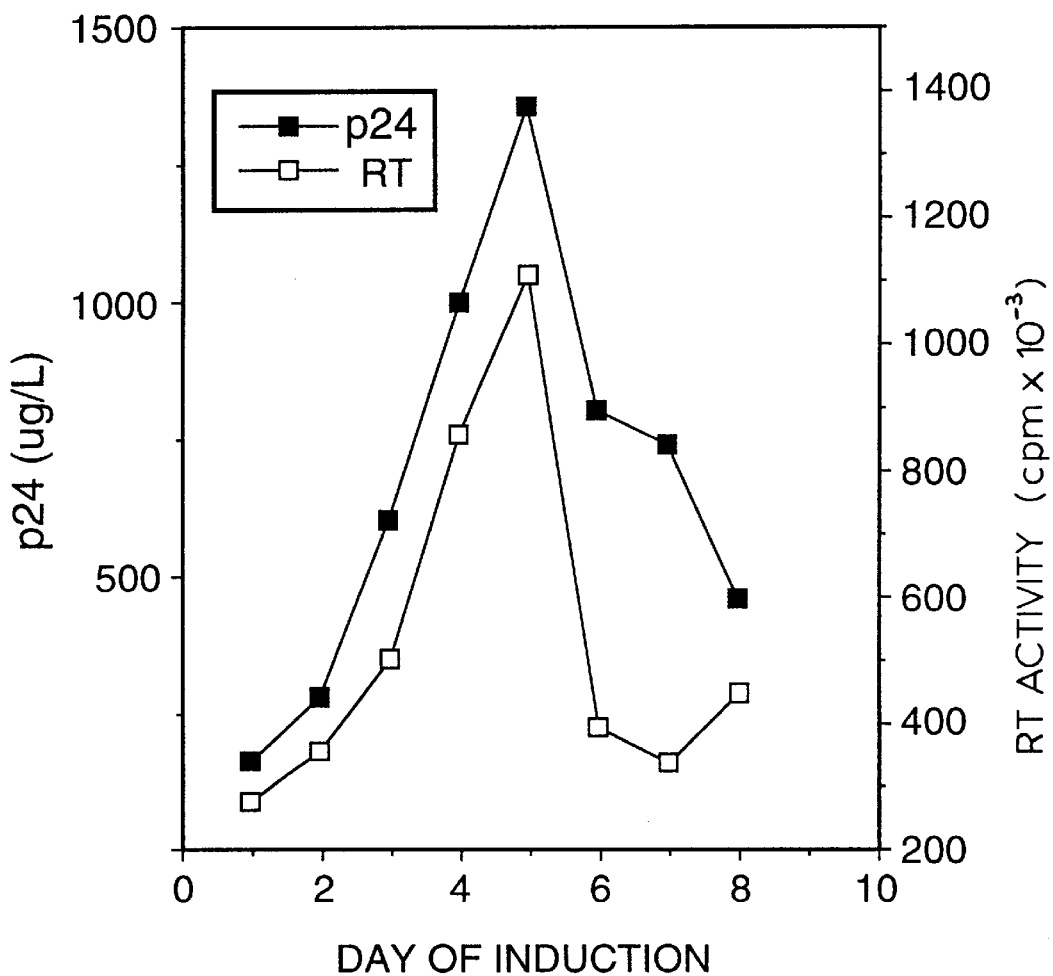
FIG. 11 depicts the distribution of RT activity and p24 antigen associated with high molecular weight material present in the supernatants of stably transfected Vero cells over a period of eight days. The cells were grown to confluence and 5 uM CdCl$_2$ was added to stimulate virus-like particle production. Every twenty four hours the culture medium was replaced with fresh medium containing 5 uM CdCl$_2$ and this process was repeated each day for eight days. After collection of the day 8 sample, RT and p24 assays were performed on all samples simultaneously.

To improve the levels of non-infectious HIV-1 particle production in engineered cell lines, an expression vector containing the human metallothionein IIa promoter and the HIV-1 protein coding DNA fragment was developed to allow for the inducible expression of virus-like particles in stably engineered cell lines (FIG. 10). After co-transfecting this vector into Vero cells along with the G418 resistance marker, numerous clones were identified which produced high levels of particulate RT activity. HIV-like particle production was verified by electron microscopy and p24 antigen assays indicated that levels of particle production were higher than normally observed in an infection of human leukaemic T-cells with infectious HIV-1. Moreover, particle production in the stably transfected Vero cells was maintained for at least eight consecutive days after reaching confluence when the cells were given fresh medium and cadmium chloride every twenty four hours. Inducible and long-term expression was not limited to monkey Vero cells.

Metal-responsive expression of substantial amounts of particles was also observed in a human colon adenocarcinoma cell line. These data indicate that a wide variety of cell lines are suitable for the large-scale production of non-infectious virus-like particles.

Although one major advantage of this method is the possibility to produce virus-like particles which may potentially contain all of the viral proteins in their native configuration, it is nevertheless possible to produce modified virus-like particles containing viral antigens with altered structures. It may be determined that the introduction of epitopes from alternative viral strains into certain regions of the HIV-1 envelope glycoprotein may enhance its immunogenicity and is of net benefit in spite of potential negative effects associated with the possible alteration of native conformational epitopes. In addition, it may be possible to improve the immunogenicity of HIV-like particles by deleting certain enhancing or immunosuppressive regions of the envelope or other viral proteins. To demonstrate the feasibility of producing virus-like particles containing modified envelope proteins, we first mutated the proteolytic processing site of the gp160 envelope glycoprotein precursor to block processing of the gp160 molecule into the mature gp120 envelope glycoprotein and the gp41 transmembrane glycoprotein. This experiment was performed to determine if unprocessed gp160 could be targeted to the membrane of virus-like particles. Since modified gp120 molecules may be easily shed from virus-like particles as a result of a reduced affinity for the gp41 transmembrane glycoprotein, it may be necessary to block proteolytic processing to efficiently retain modified envelope molecules on the particles. Sucrose density gradient analysis of particles produced from an expression construct containing a mutation in the region coding for the processing site revealed the presence of uncleaved gp160 tightly associated with RT activity in heavy molecular weight material released from transfected cells. Furthermore, additional expression constructs encoding envelope glycoproteins with epitope insertions at defined sites demonstrated the feasibility of producing particles with modified gp120 envelope glycoproteins containing specific aminoacid insertions. Conversely, deletion of DNA sequences coding for the major part of gp120 resulted in the production of virus-like particles lacking the extracellular domain of the envelope protein.

Genetically engineered, non-infectious HIV-like particles are designed to represent a completely safe candidate vaccine for use in humans. This is due to the fact that cell lines producing the virus-like particles do not contain the genetic elements required for reverse transcription. However, with the elimination of only the LTR elements, it may be argued that recombination of the protein coding sequences with heterologous LTR elements in either the vaccine-producing cell or in the vaccine recipient may result in the regeneration of an infectious retrovirus. This possibility can be completely eliminated by making a number of additional genetic modifications in regions of the HIV nucleotide sequences which are necessary for infectivity but dispensable for particle production and immunogenicity. Such regions include the RNA packaging signal, the region coding for the C-terminus of the gag p15 product, and the vif, integrase, reverse transcriptase, and tat genes. An expression construct containing mutations of this nature in addition to the deletion of the LTR elements could not give rise to infectious retrovirus, even if recombined with functional LTR elements. In the present invention, we have demonstrated that it was possible to delete 26 nucleotides between the first splice donor and the initiation codon for gag which encompasses part or all of the HIV-1 RNA packaging signal. In these experiments, virus-like particles expressed by this construct in stably transfected COS cells were indistinguishable from particles expressed from earlier constructs indicating that RNA packaging is not a critical function in the expression of non-infectious HIV-1 virus-like particles. Furthermore, we were able to show that the deletion in both the Integrase and the Vif genes did not affect particle formation.

EXAMPLES

Example 1

This Example illustrates the expression of the major HIV protein antigens in cells transfected with an HIV expression construct.

FIG. 2 shows a diagram of the expression construct termed pHIV-SV which contains a single DNA fragment containing HIV-1 protein coding information from the LAV-$1_{BRU}$ strain starting at nucleotide position 678 and ending at nucleotide position 8944. This 8.3 kb fragment was made blunt-ended using the Klenow fragment of *E. coli* DNA polymerase I and inserted into a blunt HindIII site of a Bluescript-based expression vector containing the SV40 virus early promoter and late polyadenylation site. The SV40 promoter and polyadenylation sites were obtained from commercially available cloning vectors. The pHIV-SV vector is suitable for transient expression in monkey COS cells due to the presence of the SV40 virus origin of DNA replication.

Fifteen micrograms of the plasmid pHIV-SV was transfected into COS-7 cells in a 25 cm² flask using standard calcium phosphate transfection conditions. COS cells were maintained in Dulbecco's modified Eagle's medium containing 10% fetal bovine serum. HIV protein expression was analyzed by $^3$H-leucine metabolic labelling and immune precipitation of intracellular and extracellular antigens. Twenty four hours post-transfection, the cells were labelled with $^3$H-leucine for 15 hours after which the medium was harvested and kept at 0° C. Cells were lysed by the addition of 1 mL of NP-40 lysis buffer (20 mM Tris-HCl, 150 mM NaCl, 1% Nonidet P-40, 0.5% sodium deoxycholate, 1 mM phenylmethylsulfonyl fluoride, pH 7.5) and cell lysates were held at 0° C. Supernatants and lysed cell samples were first reacted with normal human serum to clear any proteins non-specifically reacting with normal human immunoglobulins. These complexes were removed by binding to protein-A agarose. The cleared medium and cell lysate samples were subsequently reacted with a commercial human anti-HIV antiserum. HIV-specific immune complexes were isolated by binding to protein-A agarose and the bound material was subjected to SDS PAGE. Gel electrophoresis and fluorography demonstrated the expression of specific bands consistent with the p17, p24, gp41, p55, gp120 and gp160 products of HIV-1. These bands were not present in control samples from cells which were not transfected with pHIV-SV.

Example 2

This Example illustrates the sedimentation of high molecular weight material associated with reverse transcriptase activity from culture supernatants of transfected COS cells.

Plasmid pHIV-CHO-SV (FIG. 3) is similar to pHIV-SV but employs the adenovirus major late promoter and two copies of the human cytomegalovirus immediate early enhancer instead of the SV40 virus early promoter. This plasmid, pHIV-CHO-SV, has been deposited with the American Type Culture Collection, Rockville, Md., on Jul. 14, 1994 under Accession No. 75828. This plasmid also contains the SV40 virus origin of replication for transient expression analysis. The two copies of the human cytomegalovirus immediate early enhancer span the region from nucleotide position –524 to –218 which was constructed from overlapping synthetic oligonucleotides. The enhancer fragments are located upstream from the adenovirus major late promoter which is contained within a 292 bp XhoI-PvuII fragment from adenovirus-2 genomic DNA encompassing the major late promoter and the 5' end of the first exon of the tripartite leader. This 292 bp fragment was ligated to a synthetic 140 bp fragment containing the 3' end of the first leader exon, all of the second leader exon, and two thirds of the third leader exon, in a pre-spliced configuration.

Three 75 cm² flasks of COS-7 cells were each transfected with 35 micrograms of the plasmid pHIV-CHO-SV and 30 mL of the 75 mL medium supernatant was collected three days post-transfection. High molecular weight complexes were pelleted through a 20% glycerol cushion containing 50 mM Tris-HCl and 0.1 mM KCl, pH 7.8 in an SW28 centrifuge tube. Centrifugation was performed at 100,000×g for 90 minutes at 4° C. Samples from mock-transfected COS cells were included as controls. The pellet was resuspended in 30 uL of Triton X-100 lysis buffer (50 mM Tris-HCl, 100 mM NaCl, 1 mM dithiothreitol, 0.1% Triton X-100, pH 7.8) for subsequent reverse transcriptase activity analysis. One third of the resuspended sample was added to a 90 uL reaction mixture containing 40 mM Tris-HCl, 4 mM dithiothreitol, 45 mM KCl, 10 mM MgCl$_2$, 20 uCi $^3$H-dTTP (80 Ci/mmol), 50 ug poly rA, and 1 ug oligo dT at pH 7.8. This mixture was incubated at 37° C. for 30 minutes. Radioactive incorporation into trichloroacetic acid-precipitable nucleic acids indicated the presence of reverse transcriptase activity. The results presented in the following Table I show the radioactivity incorporated for each sample:

TABLE I

| Sample | CPM incorporated |
| --- | --- |
| Blank | 14,110 |
| Mock transfected | 18,053 |
| Transfected | 390,220 |
| Purified MuLV reverse transcriptase | 5,416,920 |

These data demonstrate that reverse transcriptase activity is present in a high molecular weight material released in the culture supernatants of COS cells transfected with an HIV expression plasmid.

Example 3

This Example illustrates the presence of multiple HIV-1 antigens associated with high molecular weight material released in the supernatants of transfected COS cells.

Twenty five ug of the plasmid pHIV-SV was transfected into COS cells in a 75 cm² culture flask using a commercial Lipofectin transfection kit. Eight mL of the 10 mL medium supernatant was harvested three days post-transfection and particulate material was pelleted at 100,000×g through a 20% glycerol cushion for subsequent Western blot analysis. Pellets were suspended in 100 uL of TNE (150 mM NaCl, 50 mM Tris-HCL, 1 mM EDTA, pH 7.5) prior to the addition of SDS-PAGE sample buffer and electrophoresed on a 12.5% SDS-polyacrylamide gels using standard methodologies. Proteins were electrophoretically transferred to Immobilon membranes (Millipore) for subsequent reaction with a cocktail of four monoclonal antibodies specific for gp120 (DuPont, NEA-9384), p24 (Dupont, NEA-9306), p17 (DuPont, NEA-9282) and gp41 (DuPont, NEA-9303), respectively. The second antibody was a goat anti-mouse IgG antibody conjugated to alkaline phosphatase (Promega). Antibody reactions were performed in 5% Carnation instant milk in PBS and developed using an alkaline phosphatase substrate solution (Bethesda Research Laboratories). Bands corresponding to all four HIV-1 products were present in the transfected cell samples but not observed with a control sample from mock-transfected cells. The identity of the gp41 and gp120 products was confirmed using single monoclonal antibodies in subsequent experiments.

Example 4

This Example illustrates the buoyant density analysis of HIV-like particles produced from transfected COS cells.

Figure 4:
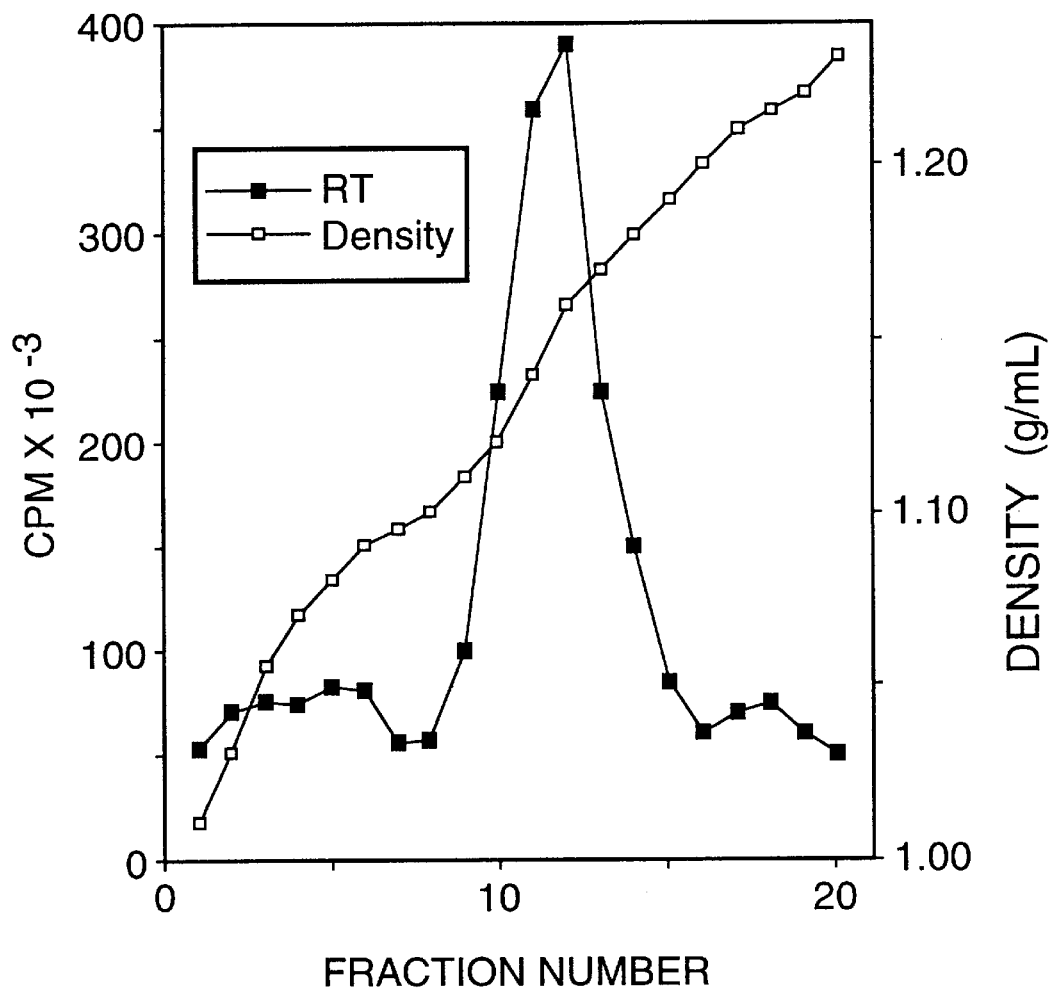
FIG. 4 shows a sucrose density gradient centrifugation profile of HIV-1-like particles expressed in transiently transfected COS cells. Fractions containing virus-like particles were identified by RT assay and the density of individual fractions was determined gravimetrically. The peak of RT activity was found in the gradient fraction which exhibited a density of approximately 1.16 g/mL.

Seventy micrograms of pHIV-CHO-SV were transfected into each of five 150 $cm^2$ flasks of COS cells using the calcium phosphate method and culture supernatants were harvested three days post-transfection. HIV-like particles were precipitated from growth medium by the addition of NaCl to 0.15 M and PEG-8000 to 9.3%, and layered on an 11 mL 20–60% sucrose density gradient in 100 mM NaCl, 10 mM Tris-HCl, 1 mM EDTA, pH 7.4. The gradient was centrifuged for 15 hours at 35,000 rpm in an SW40 rotor at 4° C. The gradient was subsequently fractionated and aliquots from individual fractions were assayed for reverse transcriptase activity after the addition of Triton X-100 to 0.2% and KCl to 0.25 mM to disrupt virus-like particles. A single peak of reverse transcriptase activity banded at a buoyant density of approximately 1.16 g/mL consistent with the production of retrovirus-like particles (FIG. 4). The density of individual fractions was measured gravimetrically to determine the density of the peak fraction.

Example 5

This Example illustrates the ability to generate stably transfected COS cell clones expressing high molecular weight material containing reverse transcriptase activity.

Figure 5:
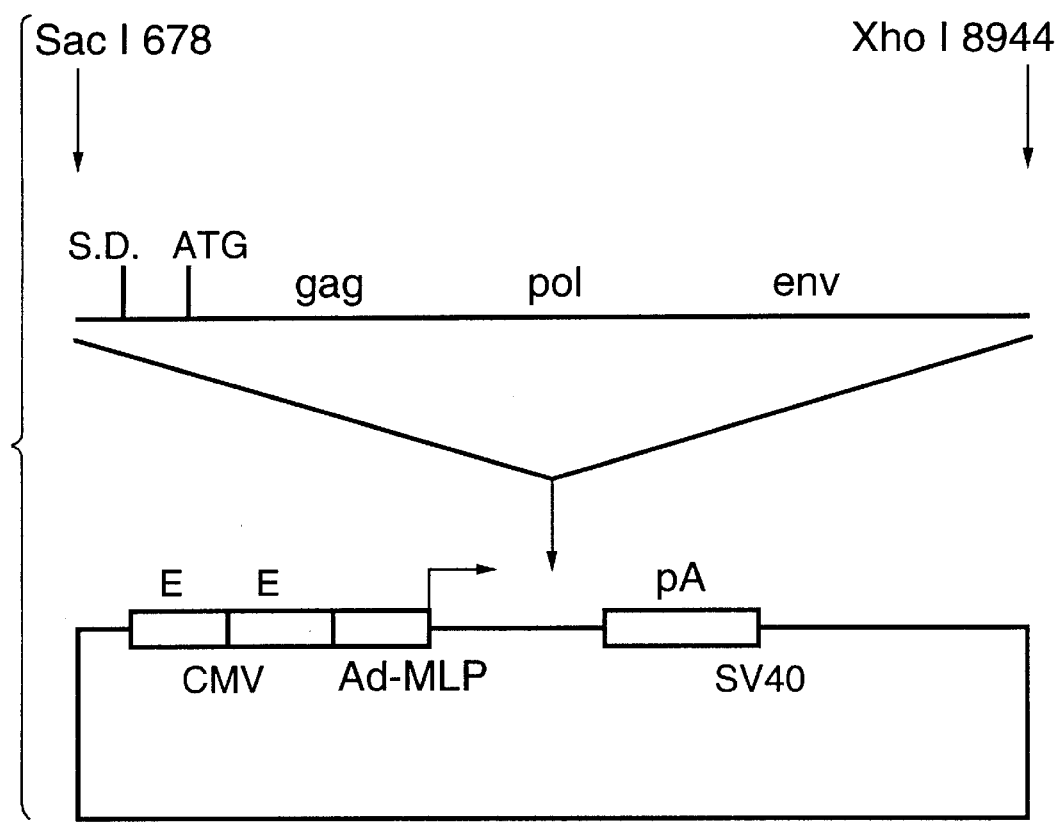
FIG. 5 shows a map of the HIV expression plasmid pHIV-Ad. This vector is similar to pHIV-CHO-SV shown in FIG. 3 but lacks the SV40 virus origin of DNA replication and was intended for stable transfection studies.

The HIV expression plasmid pHIV-Ad (FIG. 5) is similar to pHIV-CHO-SV but does not contain the SV40 virus origin of replication which would not be compatible with stable transfection in COS cells. Five ug of linear pHIV-Ad was co-transfected into COS cells in a 5 cm culture dish along with a linearised pLTRneo vector specifying resistance to the antibiotic G418. Two days following transfection, the cells were split 1:10 into medium containing 0.6 mg/mL G418 and resistant colonies were allowed to develop. Individual colonies were isolated and expanded and RT activity was measured in 8 mL supernatants from each clone as previously described. RT activity was detected in the supernatants of two of the first 44 clones. These clones continued to produce high molecular weight material associated with RT activity after continuous passage in the presence of 0.6 mg/mL of G418.

Example 6

This Example illustrates the production of HIV-like particles in stably transfected COS cells as demonstrated by Western blot analysis and sucrose density gradient centrifugation.

For Western blot analysis, a culture supernatant from stably transfected COS cells was layered over a 20% glycerol cushion and centrifuged at 100,000×g for 90 minutes to pellet virus-like particles. The pellet was resuspended in 1.5 uL of TNE for each mL of cell supernatant. Two twenty uL aliquots of the concentrated material were analyzed by Western blotting with either a commercially available human HIV-1 specific antiserum (BioRad) or a cocktail of four commercial monoclonal antibodies specific for HIV-1 gp120, gp41, p24 and p17 as described above. These results demonstrated the presence of several bands with molecular weights consistent with those of the following HIV-1 proteins: gp120, p55, gp41, p30, p23 and p17.

Figure 6:
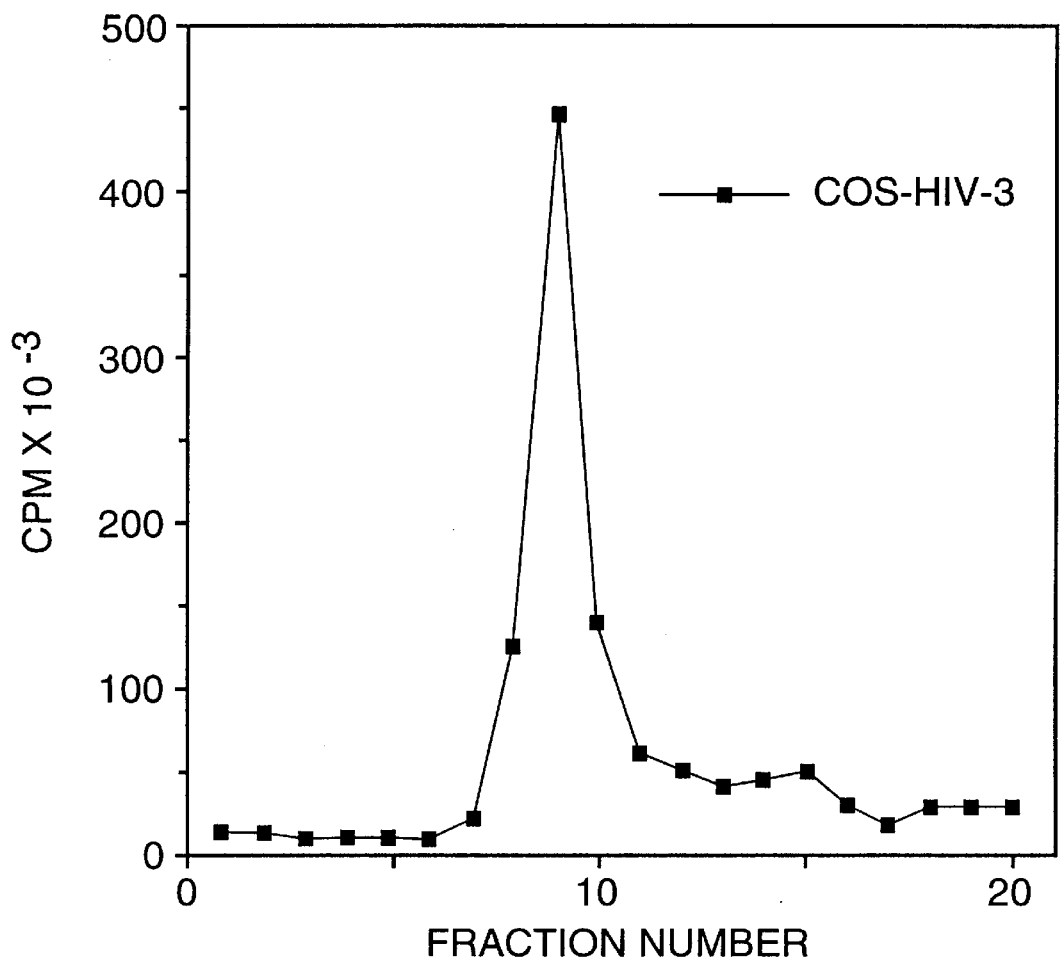
FIG. 6 shows a sucrose density gradient centrifugation profile of HIV-1 like particles expressed in stably transfected COS cells. Fractions containing virus-like particles were identified by RT assay.

For sucrose density gradient centrifugation, HIV-like particles were pelleted from a 500 mL supernatant from stably transfected COS cells by sedimentation through a 20% glycerol cushion. The pellets were resuspended in TNE and layered on a 20–60% sucrose density gradient and centrifuged as described above. After centrifugation, the gradient was fractionated and RT activity measured in each fraction. The results are shown in FIG. 6 and revealed the presence of a major peak of RT activity banding at a density consistent with the formation of HIV-like particles.

Example 7

This Example illustrates the detection of budding particles in stably transfected COS cells by electron microscopy.

For thin section analysis, stably transfected COS cells were scraped from a culture flask, washed with growth medium, and pelleted by centrifugation. Resuspended cells were fixed in 2.5% buffered glutaraldehyde, followed by 1% buffered osmium tetroxide, dehydrated through alcohol and propylene oxide and embedded in an epon-araldite epoxy resin mixture using standard techniques. Thin sections were stained with uranyl acetate and lead citrate and examined in a Philips EM3000 transmission electron microscope. The results demonstrated the presence of budding, immature particles consistent with the production of HIV-like particles.

Example 8

This Example illustrates the immunogenicity of HIV-like particles purified from stably transfected COS cells by sucrose density gradient centrifugation as described in Example 6.

Sucrose gradient fractions containing RT activity were diluted with ten volumes of TNE and virus-like particles were concentrated by centrifugation at 100,000×g for 90 minutes at 4° C. Purified virus-like particles were quantified as a function of their p24 content using commercial HIV-1 p24 assay kits (Abbott Laboratories and Coulter Immunology).

Six to eight week-old female mice, (C57BL/6×$C_3$H)F1 (Charles River, Montreal) were immunized with HIV-1 virus-like particles and serum samples were assayed for HIV-1 specific antibodies. Each mouse received two subcutaneous injections equivalent to 6 ug of p24 antigen per injection at a three week interval. The primary and boosting immunizations were performed in complete Freund's adjuvant and incomplete Freund's adjuvant, respectively. Nine days after the second immunization, sera were collected and heat-inactivated at 56° C. for 30 minutes. HIV-1 specific antibodies were detected by enzyme-immunoassays (EIAs). EIA plates (Maxisorp, Nunc) were coated with recombinant (r) antigens: rgp120 (American Biotech. Inc.), rgp160 (Repligen), rgp41 (DuPont), or rp24 (DuPont) in phosphate buffered saline (PBS, pH 7.0) at 0.4 ug per well. Adsorption of the antigens was allowed to proceed overnight at 4° C.

Unbound antigen was aspirated and the plates were blocked with 300 uL per well of 2% skim milk powder (Carnation) in PBS for two hours at room temperature. The plates were then washed three times with PBS containing 0.025% Tween 20 (BioRad). Serum samples were serially diluted in PBS and added to individual wells for one hour at room temperature. The plates were then washed three times with PBS/Tween 20 as described above. A goat anti-mouse-IgG antibody conjugated to horseradish peroxidase (Jackson Laboratories) was diluted 1 in 5000 with PBS and added for one hour at room temperature. After washing with PBS/Tween 20, 100 uL of a tetra-methylbenzidine substrate solution diluted 1 in 10 with peroxide reagent as described by the manufacturer (ADI Diagnostics) was added to each well for 10–15 minutes at room temperature. One hundred uL of 1N $H_2SO_4$ was added to stop the reactions and the plates were read in an EIA plate reader at 450 nm.

Figure 7:
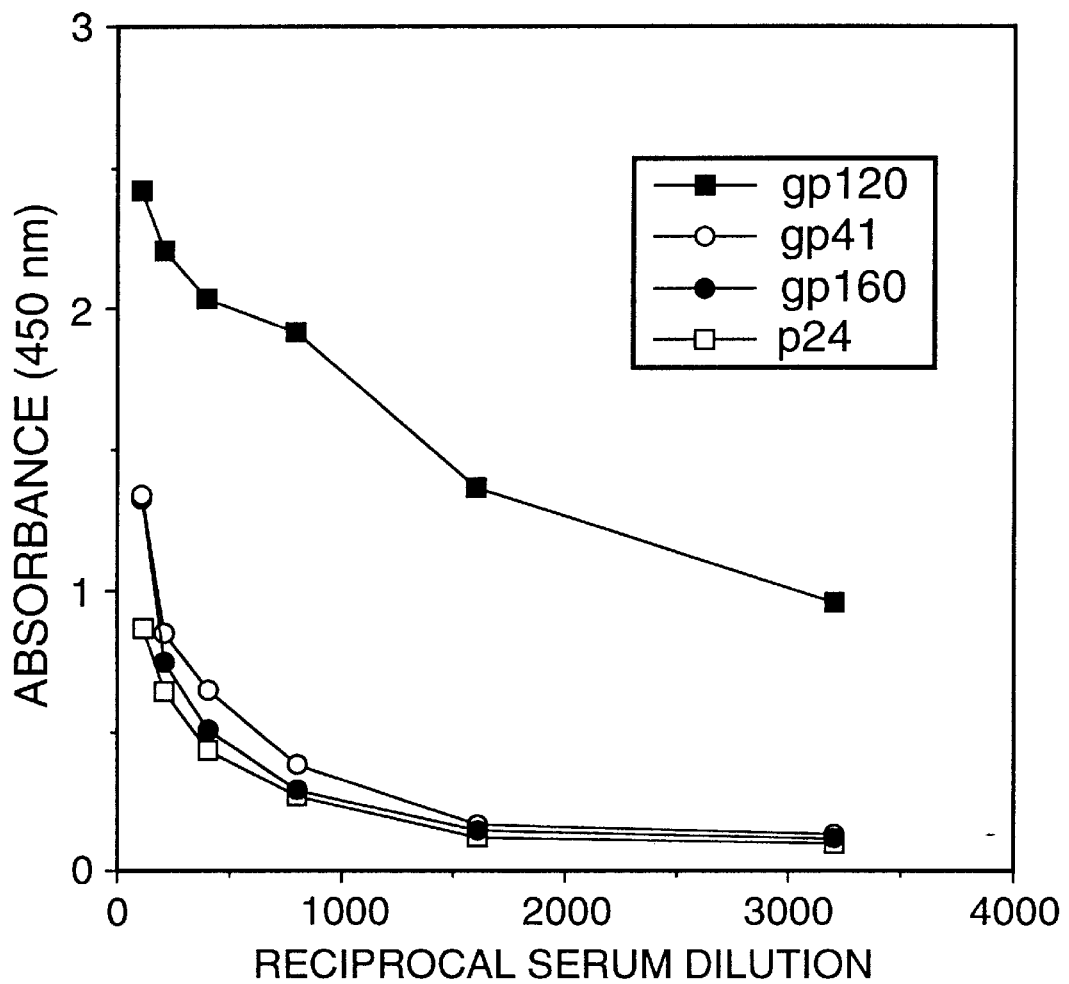
FIG. 7 represents the titration curves of IgG antibody reactivities against four recombinant HIV-1 antigens (gp120, gp160, gp41 and p24), as measured by antigen-specific EIA's. Each point is the mean of two determinations obtained independently for anti-sera collected from two mice immunized with two injections of virus-like particles. Absorbance values obtained for normal mouse serum used as a control were always less than 0.1.
Figure 8:
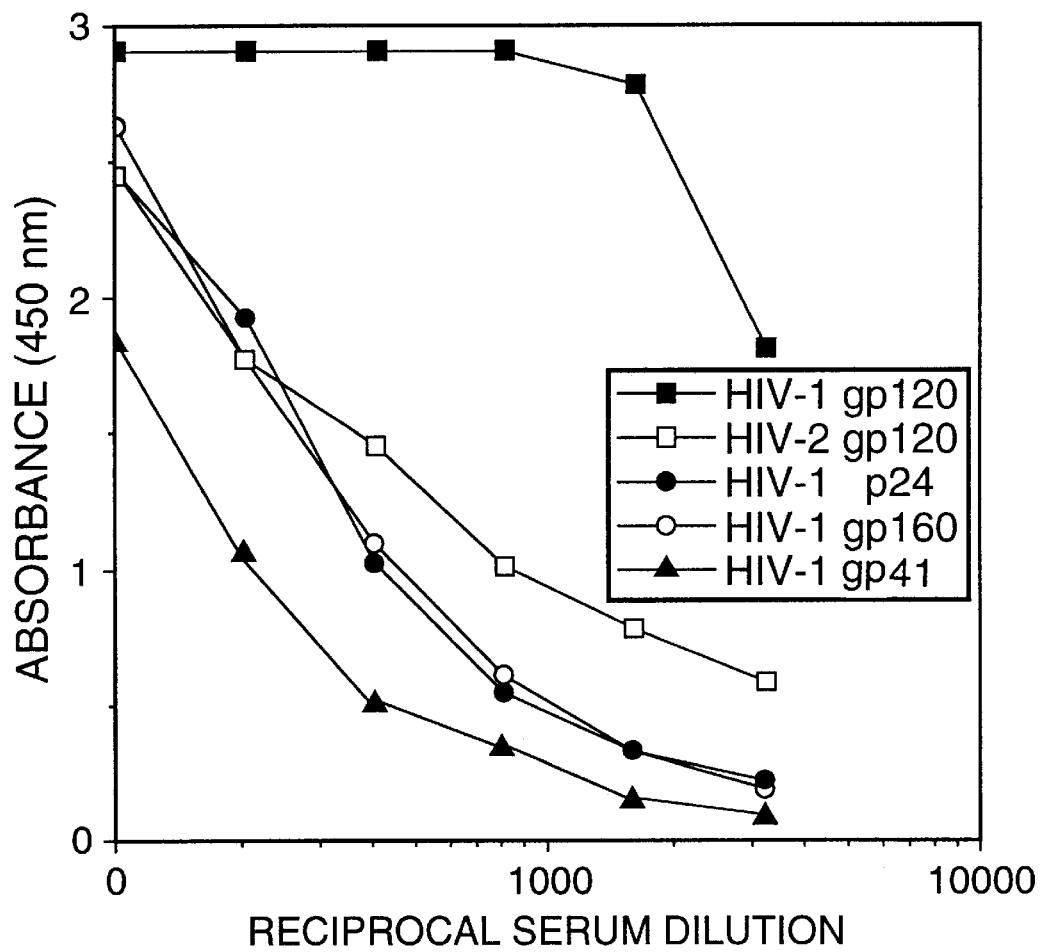
FIG. 8 represents the titration curves of IgG antibody reactivities against five different recombinant HIV-1 antigens (HIV-1 gp120, gp160, gp41, p24 and HIV-2 gp120), as measured by antigen-specific EIA's. Each point is the mean of two determinations obtained independently for antisera collected from two mice immunized with three injections of HIV-like particles. Absorbance values obtained for normal mouse serum used as a control were always less than 0.1.
Figure 9:
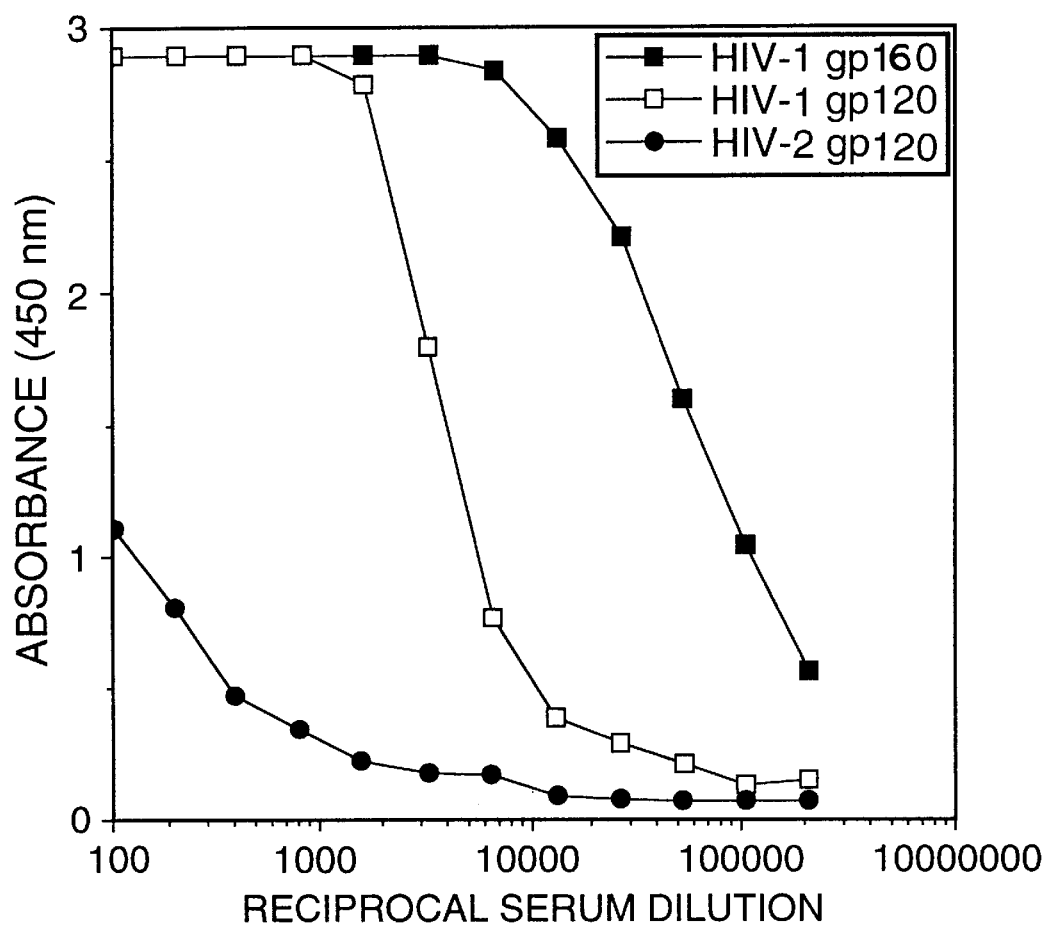
FIG. 9 represents the titration curves of IgG antibody reactivities against three recombinant HIV antigens (HIV-1 gp160 and gp120, HIV-2 gp120), as measured by antigen specific EIA's. Each point is the mean of two determinations obtained independently for antisera from two mice immunized with three injections of HIV-1-like particles. In contrast to FIG. 8, the strongest immune response was observed with HIV-1 rgp160, which was obtained from a manufacturer (Transgene) different from the one who supplied the rgp160 (Repligen) used in FIG. 8. Absorbance values obtained for normal mouse serum were always less than 0.1.

The results shown in FIG. 7 demonstrate significant IgG antibody responses against recombinant gp120, gp41, and p24 proteins. The presence of IgG antibodies against a major synthetic HIV-1 neutralization epitope encompassing residues 311 to 320 of gp120 and a synthetic gp41 B-cell epitope (Residues 727 to 751) was detected in peptide-specific EIA's using microtitre plates coated with synthetic peptides produced by solid-phase chemical synthesis on an ABI Model 430A peptide synthesizer. Murine antisera also demonstrated HIV-1 specific neutralization activity for HIV-1 strains LAV-1$_{BRU}$ and HTLV-III$_{MN}$ in a standard tissue culture syncytial inhibition assay at a serum dilution of 1/10. These results indicate that HIV-1-like particles have the capacity to induce cross-reactive immune responses against different viral isolates. Further evidence of antibody cross-reactivity was obtained with sera from animals boosted a second time with virus-like particles at 1.5 ug of p24 core antigen per dose. The IgG responses specific for various HIV recombinant antigens are shown in FIGS. 8 and 9 and demonstrate not only potent immune responses to HIV-1 gp120 and gp160, but also significant reactivity with HIV-2 gp120 as well. These data indicate that HIV-like particles may prove to be an efficient immunogen for the induction of cross-reactive immune responses.

Example 9

This Example illustrates the inducible expression of HIV-like particles following transfection of an inducible expression vector into Vero cells.

FIG. 10 shows a map of the HIV expression vector pMT-HIV which is similar to previous expression vectors but contains the human metallothionein IIa promoter from nucleotide positions −742 to +59, placed directly upstream of the HIV-1 coding sequences which begin at nucleotide position 678. This plasmid has been deposited with the American Type Culture Collection on Oct. 12, 1990 (#40912). After co-tansfection of pMT-HIV into Vero cells with the G418 resistance marker, numerous G418 resistant colonies were isolated and tested for RT production in response to cadmium chloride ($CdCl_2$) addition. Individual clones were grown to confluence in 9 cm culture dishes and treated with 5 uM $CdCl_2$ for twenty four hours, after which a standard assay for RT activity was performed on high molecular weight material pelleted from 8 mL culture supernatants as previously described in Example 2. These results demonstrated the production of significant levels of RT activity in at least 30% of the clones. RT activity in the absence of induction was detectable in the supernatants of only a few Vero cell clones. The following Table II shows the levels of p24 antigen production detected in the culture supernatants of six clones in the presence and absence of $CdCl_2$. p24 levels were measured using a commercial HIV-1 p24 assay kit and the results demonstrated a very high expression level for one clone (clone 11) and high induction ratios for all six clones.

TABLE II p24 Production in Induced and Non-Induced Vero Cell Clones

| Clone Number | Non-Induced (ug/L) | Induced (ug/L) | Ratio |
|---|---|---|---|
| 7 | <.01 | 16 | >1600 |
| 10 | <.01 | 33 | >3300 |
| 11 | .41 | 600 | 1463 |
| 30 | .02 | 33 | 1650 |
| 62 | .02 | 112 | 5600 |
| 76 | <.01 | 74 | >7400 |

Example 10

This Example illustrates the production of mature HIV-like particles in Vero cell clone 11 which was stably transfected with the inducible expression vector pMT-HIV.

Subconfluent cells grown in a 75 $cm^2$ culture flask were treated with 5 uM $CdCl_2$ for twenty four hours, then scraped from the flask and processed for thin section electron microscopy as described in Example 7. Electron micrographs showed numerous mature and immature virus-like particles budding from the plasma membrane of the transfected cells. These levels of particle formation were consistent with the high levels of p24 and RT production observed for this clone.

Example 11

This Example illustrates the continuous production of RT activity and p24 core antigen in a single flask of Vero cell clone II over an eight day period of continuous induction with $CdCl_2$.

Clone 11 cells were grown to confluence in a 75 $cm^2$ culture flask and were then treated with 5 uM $CdCl_2$ for twenty four hours after which all of the medium was harvested and fresh medium containing $CdCl_2$ added. This process was repeated every twenty four hours for eight days and the levels of RT and p24 production in each twenty four hour culture supernatant are shown in FIG. 11. The levels of production of p24 and RT activity correlated extremely well and peaked five days after the cells reached confluence.

Example 12

This Example illustrates the feasibility of producing HIV-like particles with a genetically modified envelope glycoprotein.

It is possible that structural alterations of gp120 may result in a reduction of its binding affinity for gp41, and therefore in its shedding from the surface of the particles. Mutations preventing the proteolytic processing of the gp160 envelope glycoprotein should circumvent this problem and result in the expression of uncleaved glycoprotein precursors stably associated with virus-like particles. Codon position 455 in the LAV-$1_{BRU}$ gp160 envelope glycoprotein gene encodes an arginine residue which is the site of proteolytic cleavage in the gp160 envelope glycoprotein. This codon was mutated to encode a threonine residue using a commercial M13 phage-based site-directed mutagenesis kit (Amersham) and an appropriate synthetic mutagenic oligonucleotide complementary to the regions flanking this codon. This mutation was created in a cloned subfragment of the envelope glycoprotein gene which was subsequently used to replace the corresponding region in the pHIV-SV particle expression plasmid. Transfection of this modified plasmid into COS cells resulted in the expression of high molecular weight virus-like material in association with the gp160 envelope glycoprotein precursor as detected by Western blot analysis. The fact that gp120 was not detected was consistent with the disruption of proteolytic processing. That the gp160 envelope protein remains associated with virus-like particles was demonstrated by banding particles produced in a transient transfection experiment by sucrose density gradient centrifugation. Western blot analysis demonstrated that the gp160 precursor protein was found only in gradient fractions containing RT activity and not in heavier or lighter fractions.

The feasibility of modifying the structure of the gp120 envelope glycoprotein was further demonstrated by inserting two pairs of synthetic oligonucleotides into the BglII site at nucleotide position 7008 in the LAV-1$_{BRU}$ DNA sequence. Insertion of these oligonucleotides resulted in a modified coding sequence in which the inserted element encoded the HTLV-III$_{MN}$ V3 neutralization epitope encompassing amino acid residues 306 to 329 of the viral envelope glycoprotein. The resultant sequence encoded the complete LAV-1$_{BRU}$ envelope glycoprotein with an MN strain V3 loop insertion at amino acid position 272. The resulting plasmid is termed pV3Bg and has been deposited with the American Type Culture Collection on Oct. 12, 1990 (#40910). The oligonucleotides used in the modification were as follows:

```
5' GATCTCGGACCGCCTACAATAAAAGAAAAAGGATACATATAGGA 3'
3' AGCCTGGCGGATGTTATTTTCTTTTTCCTATGTATATCCTGGTCCCTC 5'  (SEQ ID NO:1)

5' CCAGGGAGAGCATTTTATACAACAAAAAATATAATAGGAACGCGTA 3'
   3' TCGTAAAATATGTTGTTTTTTATATTATCCTTGCGCATCTAG 5'  (SEQ ID NO:2)
```

Western blot analysis of pellets obtained by centrifugation of transfected cell supernatants through a 20% glycerol cushion demonstrated the production of particulate material containing gp120 at a level similar to that observed with the unmodified expression vector. These data demonstrate that the insertion of 24 additional aminoacid residues at amino acid position 272 of the LAV-1 envelope did not disrupt its targeting to the viral membrane, the processing of the envelope glycoprotein precursor, or its non-covalent association with the gp41 transmembrane glycoprotein. It is therefore likely that additional gp120 alterations might be tolerated and, thus, allow for further modulation of the immunogenicity of the envelope glycoprotein.

Example 13

This Example illustrates the feasibility of creating a mutation in an HIV-1 sequence element which is required for infectivity but dispensable for virus-like particle production.

Figure 12:
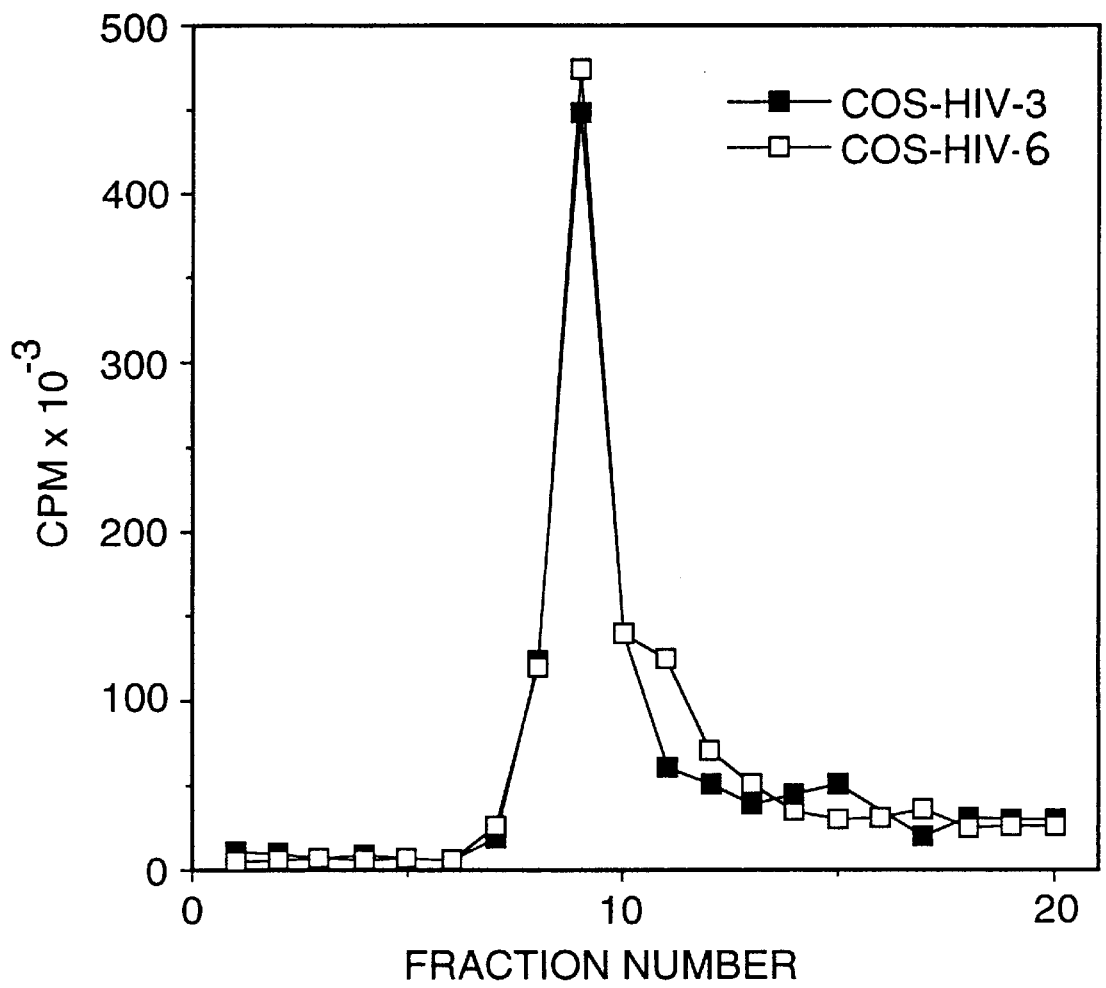
FIG. 12 shows the sucrose density gradient centrifugation profiles for HIV-1-like particles prepared from two lines of stably transfected COS cells. COS-HIV-3 was derived by transfection of COS cells with the pHIV-Ad expression vector and COS-HIV-6 was derived by transfection with a similar vector containing a 26 bp deletion in the RNA packaging signal sequence.

To demonstrate the feasibility of producing HIV-like particles using an expression construct containing an additional mutation in a genetic element required for infectivity, an expression plasmid containing a deletion of the RNA packaging signal was created. This signal has been shown to lie between the first splice donor at nucleotide position 744 and the initiation codon for Gag at nucleotide position 790 and to be critical for HIV RNA packaging and infectivity. This region was deleted from a clone containing an 8.9 kb SacI-SacI fragment of LAV-1$_{BRU}$ (nucleotide positions 678–9619) by removing a 114 bp SacI-HgaI restriction fragment encompassing nucleotide positions 678 to 791. The deleted fragment was replaced with a double-stranded synthetic fragment containing a deletion of 26 bp from nucleotide positions 753 to 777. The modified SacI-SacI fragment was then used as a source of DNA to isolate the SacI-XhoI fragment (nucleotide positions 678 to 8944) for construction of an HIV expression vector utilizing the adenovirus major late promoter similar to pHIV-Ad described in Example 5. The new plasmid, termed pHIV-Ad-d26 was transfected into COS cells as described in Example 5 and G418 resistant clones constitutively expressing RT activity were isolated. Virus-like particles were pelleted from 200 mL of culture supernatants from two COS cell clones stably transfected with the original and "RNA packaging-deleted" expression constructs, respectively. FIG. 12 shows a comparison of the sucrose density gradient centrifugation profiles for the virus-like particles derived from these expression constructs. Virus-like particles derived from the construct containing the packaging deletion were not significantly different from those derived from the original expression construct.

Example 14

This Example illustrates the production of non-infectious SIV-like particles.

To demonstrate the applicability of this invention to the production of virus-like particles derived from a retrovirus other than HIV, an SIV expression vector containing a DNA fragment from the provirus of SIV$_{mac239}$ was constructed.

Although the nucleotide sequence of the SIV$_{mac239}$ provirus has yet to be published, comparison of its restriction map with that of SIV$_{mac142}$ which has been sequenced revealed a number of similarities. The NarI restriction site at nucleotide position 835 of SIV$_{mac142}$ and the two SstI restriction sites at positions 5756 and 9236 are conserved in the SIV$_{mac239}$ provirus. Therefore, two fragments from the SIV$_{mac239}$ provirus consisting of the 4.9 kb NarI-SstI and the 3.4 kb SstI-SstI fragments were isolated from the cloned SIV$_{mac239}$ provirus and inserted into an expression vector utilizing the SV40 virus early promoter as described in Example for LAV-1$_{BRU}$. Transfection of this plasmid, termed pSIV-SV, into COS cells resulted in the transient expression of RT activity as described for LAV-1$_{BRU}$ also in Example 2. The co-transfection of Vero cells with pSIV-SV and a G418 resistance marker resulted in the isolation of drug resistant clones constitutively expressing RT activity as described in Example 5 for the transfection of pHIV-Ad into COS cells.

To provide further evidence for the production of SIV-like particles, culture supernatants were collected from Vero cells stably transfected with pSIV-SV and virus-like particles were pelleted by centrifugation at 100,000×g. Pelleted material was analyzed by SDS-PAGE and Western blotting using a monkey SIV-specific antiserum. Analysis of the data revealed the presence of several bands with molecular weights consistent with the expression of the major SIV antigens. These bands were not detected in the culture fluid of non-transfected Vero cells.

Example 15

This Example illustrates the feasibility of expressing HIV-like particles using an expression vector containing a deletion of the provirus genome which encodes proteins required for viral infectivity but which are dispensable for particle assembly.

The pMT-HIV expression vector described in Example 9 was modified to contain a deletion of the 26 nucleotides in the RNA packaging region as described in Example 13. A further deletion of HIV coding sequences which encode the Vif and Integrase genes was also performed. The Vif and Integrase genes are required for viral infectivity but are dispensable for particle assembly. This second deletion was accomplished by removing a 746 bp fragment between the BspmI restriction sites at nucleotide positions 4345 and 5091 of the LAV-1$_{BRU}$ genome. The resultant expression plasmid, termed pMT-HIV-dVI-d26, has been deposited with the American Type Culture Collection on Oct. 12, 1990 (#40911). Transfection of pMT-HIV-dVI-d26 into COS cells in a transient expression assay resulted in the expression of significant quantities of p24 antigen in the culture supernatant but no RT activity was detected. The absence of RT activity indicates that the neighbouring integrase mutations may have affected RT protein processing. Evidence for the assembly of virus-like particles was obtained from a Western blot analysis of material pelleted from the culture supernatant of transfected cells by high speed centrifugation through a 20% glycerol cushion which demonstrated the presence of gp120 in significant quantities. Production of p24 and gp120 was not detected in the culture supernatant of non-transfected cells.

Example 16

This Example illustrates the production of HIV-like particles which are deficient in the gp120 envelope glycoprotein due to a deletion of gp120 coding sequences in a modified expression vector.

The HIV expression vector pHIV-SV was modified so as to encode the production of virus-like particles lacking the gp120 envelope glycoprotein. This was accomplished by deleting a fragment between the KpnI site at nucleotide position 6379 and the BglII site at nucleotide position 7668. The remaining restriction ends were treated with Klenow DNA polymerase to remove the 3' overhang at the KpnI end and to fill in the 5' overhang at the Bgl II end. The blunt ends were ligated to a BglII linker (Pharmacia, 5'-pd [CAGATCTG]-3') which was then cleaved with BglII and the sticky ends were ligated together. This ligation restored what remained of the gp120 reading frame to allow for the later insertion of heterologous coding sequences. This plasmid, termed pBL-HIV-dgp120-6, has been deposited with the American Type Culture Collection on Oct. 12, 1990 (#40913).

Transfection of pBL-HIV-gdp120-6 into COS cells in transient expression assays resulted in the expression of high molecular weight material containing RT activity. Western blot analysis of the pellet obtained by high speed centrifugation of the culture supernatant through a 20% glycerol cushion revealed the expression of the p24 and p17 gag proteins but not of gp120. In a control experiment where the original pHIV-SV expression plasmid was transfected, significant quantities of HIV-1 gp120 were detected in the pelleted fractions.

SUMMARY OF DISCLOSURE

In summary of this disclosure, the present invention provides enetically-engineered non-infectious and immunogenic retrovirus-like particles which are candidates for vaccines against the respective retroviruses, such as AIDS and procedures for producing the same. Modification are possible within the scope of this invention.

---

What we claim is:

1. A genetically-engineered, non-infectious, non-replicating and immunogenic retrovirus-like particle comprising the gag, pol and env proteins of the human immunodeficiency virus wherein said proteins are encoded by a modified human immunodeficiency virus genome devoid of long terminal repeats and comprising gag, pol and env genes of the human immunodeficiency virus substantially in their natural conformation.

2. The particle of claim 1 which is deficient in primer binding site.

3. The particle of claim 1 which is deficient in Integrase and Vif proteins.

4. The particle of claim 1 wherein a V3 neutralizing epitope from a heterologous HIV isolate is inserted into a BglII site of the envelope glycoprotein.

5. A genetically-engineered, non-infectious, non-replicating and immunogenic retrovirus-like particle comprising gag and pol proteins of the human immunodeficiency virus, wherein said proteins are encoded by a modified human immunodeficiency virus genome devoid of long terminal repeats and comprising gag and pol genes of the human immunodeficiency virus substantially in their natural conformation.

6. An immunogenic composition capable of eliciting HIV-specific antibodies, comprising a retrovirus-like particle as claimed in any one of claims 1, 2, 3, 4, and 5 and a physiologically-acceptable carrier therefor.

7. The particle of claim 5 wherein said modified human immunodeficiency virus genome is contained in an expression vector.

8. The product of claim 7 wherein said expression vector is plasmid pBL-HIV-dgp120-6.

* * * * *